(12) United States Patent
Metwally

(10) Patent No.: US 10,386,353 B1
(45) Date of Patent: Aug. 20, 2019

(54) SERIAL CHEMICAL EXTRACTION AND SPECTROMETRIC ANALYSIS SYSTEM

(71) Applicant: Omar Nabil Metwally, San Francisco, CA (US)

(72) Inventor: Omar Nabil Metwally, San Francisco, CA (US)

( * ) Notice: Subject to any disclaimer, the term of this patent is extended or adjusted under 35 U.S.C. 154(b) by 247 days.

(21) Appl. No.: 15/632,934

(22) Filed: Jun. 26, 2017

(51) Int. Cl.
*G01N 33/00* (2006.01)
*B01D 11/02* (2006.01)
*G01N 1/40* (2006.01)

(52) U.S. Cl.
CPC ..... *G01N 33/0098* (2013.01); *B01D 11/0288* (2013.01); *G01N 1/4055* (2013.01); *G01N 1/4077* (2013.01); *G01N 2001/4061* (2013.01); *G01N 2001/4088* (2013.01)

(58) Field of Classification Search
USPC .......................................... 422/501, 509, 527
See application file for complete search history.

(56) References Cited

U.S. PATENT DOCUMENTS

| 4,935,020 A | * | 6/1990 | Broden | B01L 3/0217 422/923 |
| 2003/0183020 A1 | * | 10/2003 | Kipke | B01F 5/0646 73/863 |
| 2007/0269355 A1 | * | 11/2007 | Malmqvist | B01F 5/0685 422/224 |
| 2016/0209393 A1 | * | 7/2016 | Dimson | G01N 33/487 |

* cited by examiner

*Primary Examiner* — Nina Bhat

(57) ABSTRACT

The system includes an infusion chamber to receive a selected amount of extraction solvent and a sample to be analyzed. The reagents are incubated in the infusion chamber, which is sealed at both ends by rubber stoppers and filter baskets. The reagents are agitated and incubated at the desired temperature for a specified length of time. One end of the infusion chamber is then replaced with a filter-funnel assembly, and a plunger is slidingly received in the opposite end of the infusion chamber to pressurize it and expel the contents of the infusion chamber. The filter-funnel assembly holds back solid matter while allowing the solution to pass through a funnel and either into a spectrometric cuvette. Spectrometry is used to identify compounds, varieties of *cannabis*, and calculate potencies of edible *cannabis*-infused products. This system serializes the infusion, extraction, filtration, spectroscopic analysis and can be operated by non-experts.

1 Claim, 6 Drawing Sheets

Absorbance and Transmittance of Sample #1

| Wavelength (nm) | Absorbance Solution #1 | Transmittance Solution #1 |
|---|---|---|
| 379.801 | 0.01 | 99.99 |
| 380.064 | 0.1 | 99.9 |
| 400.961 | 0.3 | 99.7 |
| 401.244 | 0.05 | 99.95 |
| 401.527 | 0.07 | 99.93 |
| 596.168 | 0.2 | 99.8 |
| 605.735 | 9.00E-02 | 9.99E+01 |
| 700.566 | 1.50E-01 | 9.99E+01 |
| 800.092 | 0 | 100 |
| 900.101 | 0 | 100 |
| 900.329 | 0.1 | 99.9 |
| 950.284 | 0 | 100 |

Figure 6

SERIAL CHEMICAL EXTRACTION AND SPECTROMETRIC ANALYSIS SYSTEM

FIELD OF THE INVENTION

The present invention generally relates to equipment and methods for use in the extraction and analysis of chemical compounds in *cannabis* flower and edible *cannabis*-containing products. More particularly it relates to a method and an apparatus capable of being used for extracting cannabinoids and other chemical compounds in plant matter or edible *cannabis*-infused products. The solutes contained within the solid matter are extracted through an infusion process analogous to steeping tea or brewing coffee. Organic solvents such as alcohols and hydrophobic molecules effectively dissolve cannabinoids and other psychoactive and physiologically active compounds in *cannabis* flowers. These cannabinoid-containing solvents can then be used to prepare edible *cannabis* products, or they can be analyzed using light spectrometry to determine the identities of flower varieties and calculate potencies of edible *cannabis*-infused products. The filter-funnel assembly separates the residual solid matter from the cannabinoid-containing solvent and directs the solution either into a receptacle or into a cuvette where it can be analyzed with light spectrometry for chemical composition and potency.

DESCRIPTION OF THE RELATED ART

The psychoactive and physiologically active compounds in indica and *sativa* species of the *Cannabis* genus can be ingested through non-inhaled means such as edible and topical *cannabis*-infused products. Such extractions can be performed in home kitchens and commercial facilities to yield *cannabis*-infused beverages, oils, and butters, pastries, cosmetics, and other food and health products. While commercially available products are produced under a controlled environment, cottage businesses, hobbyists, and medical marijuana patients cannot reliably analyze the quality and potency of their *cannabis*-containing products due to the prohibitive cost of current analytical methods.

Spectrometry is a method of analyzing the chemical composition, identity and potency of *cannabis* flowers and of *cannabis*-containing edible products. Unlike other methods of analyzing the composition and potency of *cannabis* products, such as gas chromatography and mass spectrometry, light spectrometry (including ultraviolet, visible light, and infrared spectrum light) does not destroy the analyzed sample and is less financially prohibitive for consumers and producers of *cannabis* products. Light spectrometry also does not require a high level of scientific expertise to operate. Infrared light spectrometry has gained popularity in recent times because absorbance patterns of infrared light are modulated by the unique chemical bonds in molecules. Cannabinoids are known to absorb and emit light in the near-ultraviolet range. Light spectrometry generates a unique profile of a *cannabis* flower's psychoactive and physiologically active compounds.

Technical Problem

Many methods of chemical analysis, including spectrometry, necessitate preparation of a sample through an extraction process in which soluble, psychoactive and non-psychoactive compounds are extracted with a solvent, and the cannabinoid-containing solution is separated from the residual solid matter. The cannabinoid-containing solution can then be consumed directly, stored, incorporated into edible and health products, and analyzed for composition and potency. Individual plant varieties have also been identified through molecular probes and genetic sequencing methods, which also entail the chemical extraction of compounds of interest.

The extraction methods described above necessitate precise measurements of volumes and masses and require the operator to perform extractions under a controlled environment. The ambient light, temperature, reaction time, and energy expended to agitate the solution are all variables that influence the yield of an extraction. The composition of the sample and the solvent or solvents used also affects the quality of the extraction. Extraction protocols entail separate steps to infuse samples with solvents, sometimes incubating a mixture for a period of time at a certain temperature, agitating the mixture, and filtering the mixture to yield a cannabinoid-containing solution. The solution must be poured into a cuvette in order to be analyzed spectrometrically. These steps must then be repeated for each extraction, and all of the equipment cleaned between each extraction.

Solution to the Problem

To facilitate the extraction process, there is a need for a system that (a) streamlines these sequential steps under a controlled environment, (b) yields reproducible results, and (c) can easily be cleaned between extractions. The entire process can be serialized and the apparatus can be used for infusion, agitation, filtration, preparing a cuvette for analysis, and analyzing a sample for potency and composition using light spectrometry.

SUMMARY OF THE INVENTION

The present invention provides an extraction process apparatus, extraction method, and chemical analysis method that overcomes many of the obstacles of currently used laboratory and in-home analytical methods.

In this embodiment, the present invention is an apparatus for using a solvent to extract solutes from plant matter or edible products of interest through serial infusion, extraction, filtration, and analysis while facilitating clean-up of the apparatus between each extraction and analysis. This embodiment includes: (a) a graded cylindrical container adapted to contain an extraction reaction and which slidingly receives a plunger at one end and which can be sealed at both ends through a twist-on, twist-off capping mechanism (b) a filter-funnel apparatus with a basket that receives a rubber stopper or filter to allow agitation/infusion or filtration of the mixtures, respectively, and which can be attached and detached from the infusion chamber with a twisting motion, and which holds a detachable cuvette, (c) a plunger received by the infusion chamber and which serves the purpose of pressurizing the infusion chamber, ending the extraction reaction, and expelling the solution through the filter and compressing residual solid matter against a filter so it can be easily discarded, (d) the use of light spectrometry to measure absorbance and transmittance across ultraviolet, visible light, and infrared spectra, and any permutations of these spectra, (e) comparing absorbance spectra of samples to reference absorbance spectra and using mathematical methods to infer concentrations of certain compounds, (f) comparing absorption spectra from sample in (d) to reference absorbance and transmittance spectra and using Beer's Law and mathematical methods such as unsupervised and supervised machine learning to identify varieties of marijuana flowers for forensic, medical or recreational purposes, where steps (d), (e) and (f) are optional.

In a variety of this embodiment of the present invention, the filter-funnel's basket receives a coin-shaped rubber stopper and twists onto both ends of the infusion chamber, creating a waterproof seal that allows the agitation and infusion of a sample with solvent.

In another variation of this embodiment of the present invention, the filter-funnel component's basket end which receives a filter or rubber stopper is made of a porous mesh of varying diameter to allow faster or slower filtration rates and to filter for compounds of particular molecular properties.

In another variation of this embodiment of the present invention, a filter basket without a funnel attaches to both ends of the infusion chamber to create a waterproof seal that allows the agitation and infusion of a sample with solvent.

In another variation of the present invention, the basket end of the filter-funnel component receives a disposable or reusable filter composed of paper or other natural or synthetic materials, wherein the chemical composition of each of these filters influences the quality of the extraction reaction's yield.

In another variation of the present invention, the infusion chamber is made of an insulating material that facilitates extraction reactions at hot or cold temperatures.

In another variation of the present invention, the device can be used to extract and analyze the composition and potency of other plant-based compounds such as vitamins and physiologically active compounds.

In another variation of the present invention, light spectrometry is used to measure absorbance and transmittance of the solution yielded from the extraction reaction at the 385 nm wavelength and compared to absorption and transmittance of reference samples at the same wavelength to infer potency and composition of the sample of interest.

In another embodiment of the present invention, light at other wavelengths, including ultraviolet, visible, and infrared light, is used to calculate absorbance and transmittance of samples compared to references to infer potency and chemical composition.

In another embodiment of the present invention, a thermometer reads the temperature of the infusion chamber and displays the value on an attached screen.

In yet another embodiment, a Bluetooth, Wifi, and/or USB-enabled microcontroller transmits absorbance/transmittance spectra data points to a server, personal computer, phone or tablet, where further processing allows identification of plant varieties and their composition, and the composition and potency of *cannabis*-containing edible products, and the results of these calculations visualized on a screen.

BRIEF DESCRIPTION OF THE DRAWINGS

FIG. 6 is a vector representation of the absorbance spectra obtained from distinct *cannabis* varieties and serves as the raw data used in clustering algorithms.

DESCRIPTION OF THE PREFERRED EMBODIMENT

Figure 1:
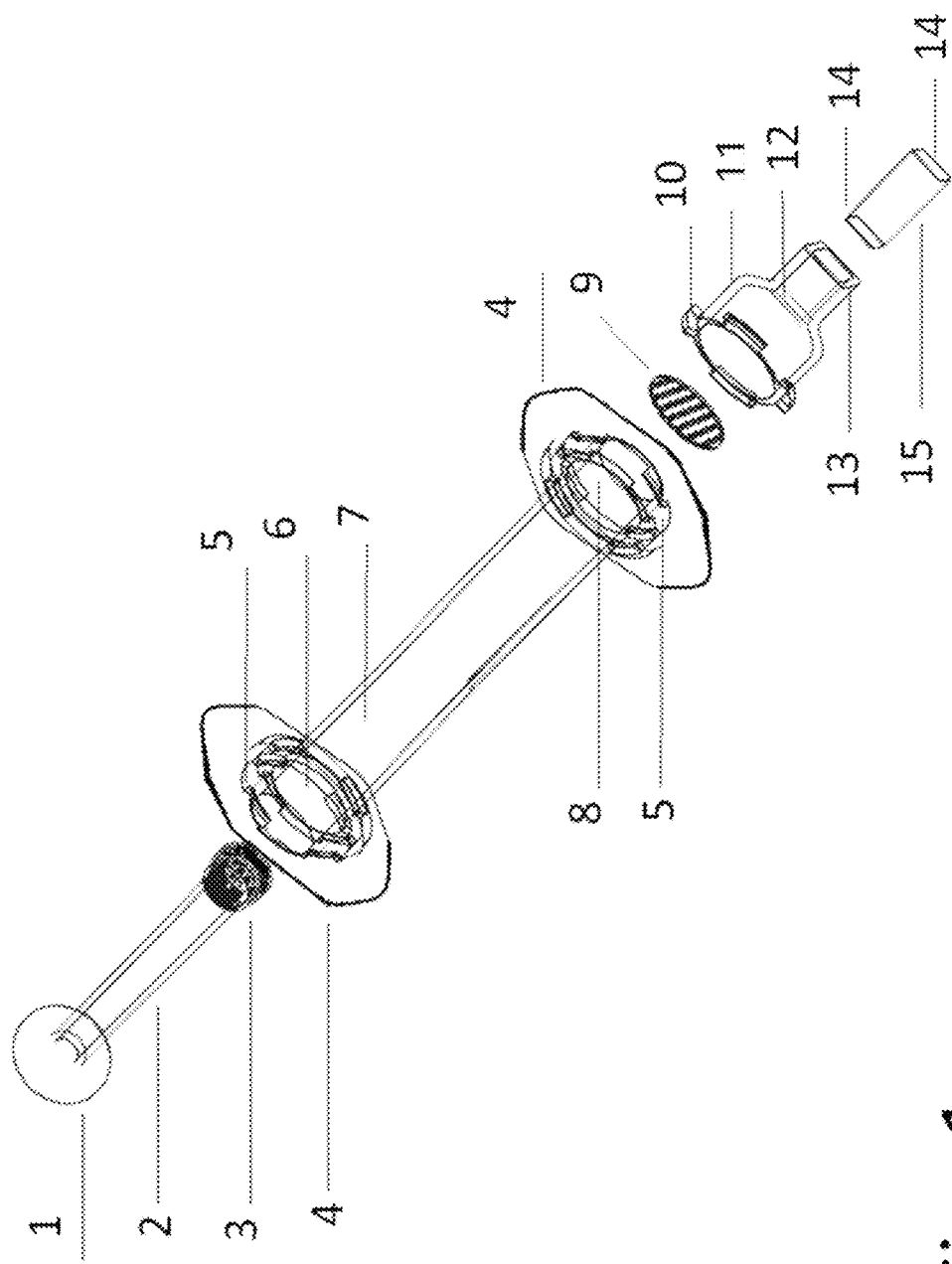
FIG. 1 is a perspective view of an embodiment of the present invention when the plunger has been inserted into one end of the infusion chamber and a filter-funnel assembly holding a filter and a cuvette has been attached to the opposite end.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. The present invention generally relates to equipment and methods for extracting and analyzing cannabinoids. More particularly, it relates to a method and an extraction device capable of being used for extracting psychoactive and physiologically active compounds from *cannabis* flowers and *cannabis*-infused products using solvents, which can then be consumed, manufactured further into edible and health products, and analyzed for potency and composition. The extraction reaction entails infusing *cannabis* flower or *cannabis*-containing edible products with a solvent such as alcohol or oils in a waterproof infusion chamber, agitating the mixture repeatedly, and filtering the residual solid matter through a funnel that directs the solvent into a receptacle or a spectrometry cuvette. Various cannabinoids, including tetrahydrocannabinol, delta-9-tetrahydrocannabinol, cannabidiol, and aromatic compounds called terpenes which may also have therapeutic effects, are soluble to varying degrees in alcohols and hydrophobic solvents. How well the mixture is agitated, how finely the solid sample is ground, the temperature of the extraction reaction, and the reaction time modulate the yield of extraction.

When performed under controlled and consistent conditions, the extraction reaction yields consistent results. The infusion chamber 7 can be made of glass, metal, plastic, ceramic, and other natural or synthetic materials that allow the operator to conduct extraction under a controlled environment. The infusion chamber can also be made of materials of varying opacity and capacity to block radiation which can degrade the solutes of interest. The insulating properties of the infusion chamber's material allow the entire apparatus to be placed in a hot or cold environment, and its insulating properties allow it to receive solvents that have been heated or cooled to a particular temperature while minimizing thermal energy transfer. The filter-funnel 11 component illustrated in FIG. 1 has a mesh basket 12 that can hold a coin-shaped rubber stopper 16 or a filter 9, creating a sealed system closed at both ends by such a rubber stopper 16. This sealed infusion chamber prevents spillage of solvent while the mixture is agitated manually or mechanically and incubated, eliminating the need for separate infusion and filtration processes and equipment.

Figure 2:
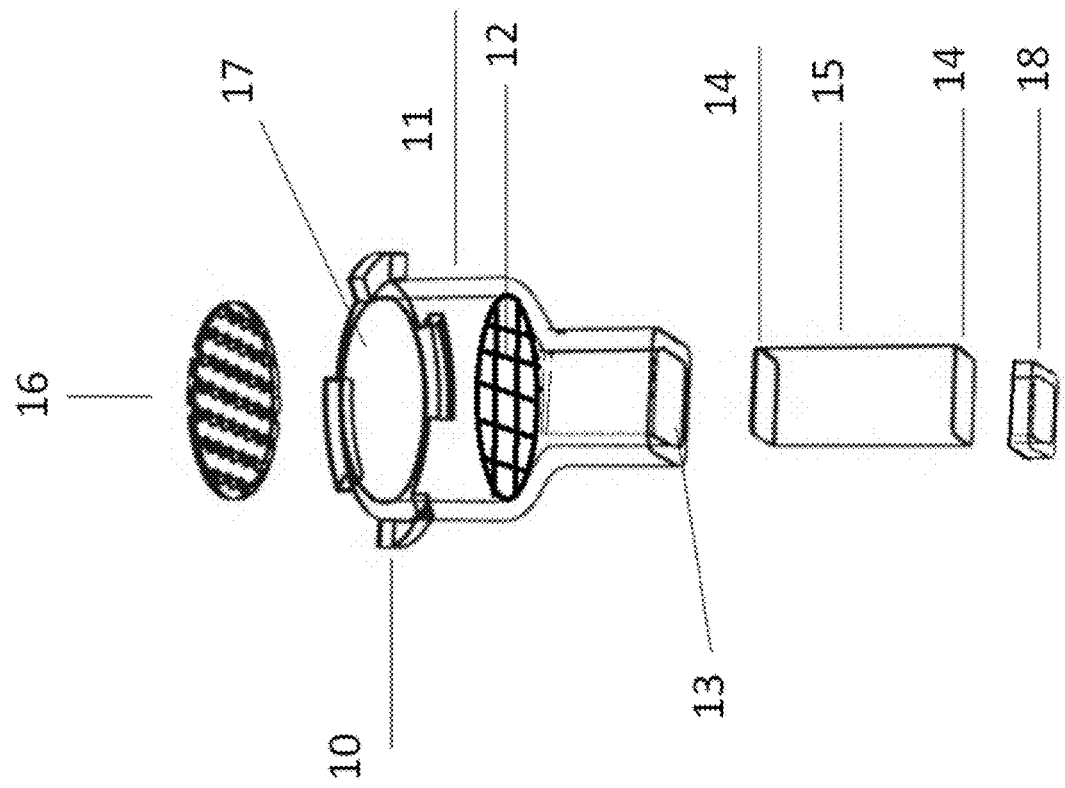
FIG. 2 is an exploded, perspective view of an embodiment of the present invention in which two filter-funnel assemblies hold coin-shaped rubber stoppers and attach to both ends of the infusion chamber to create a waterproof seal.
Figure 3:
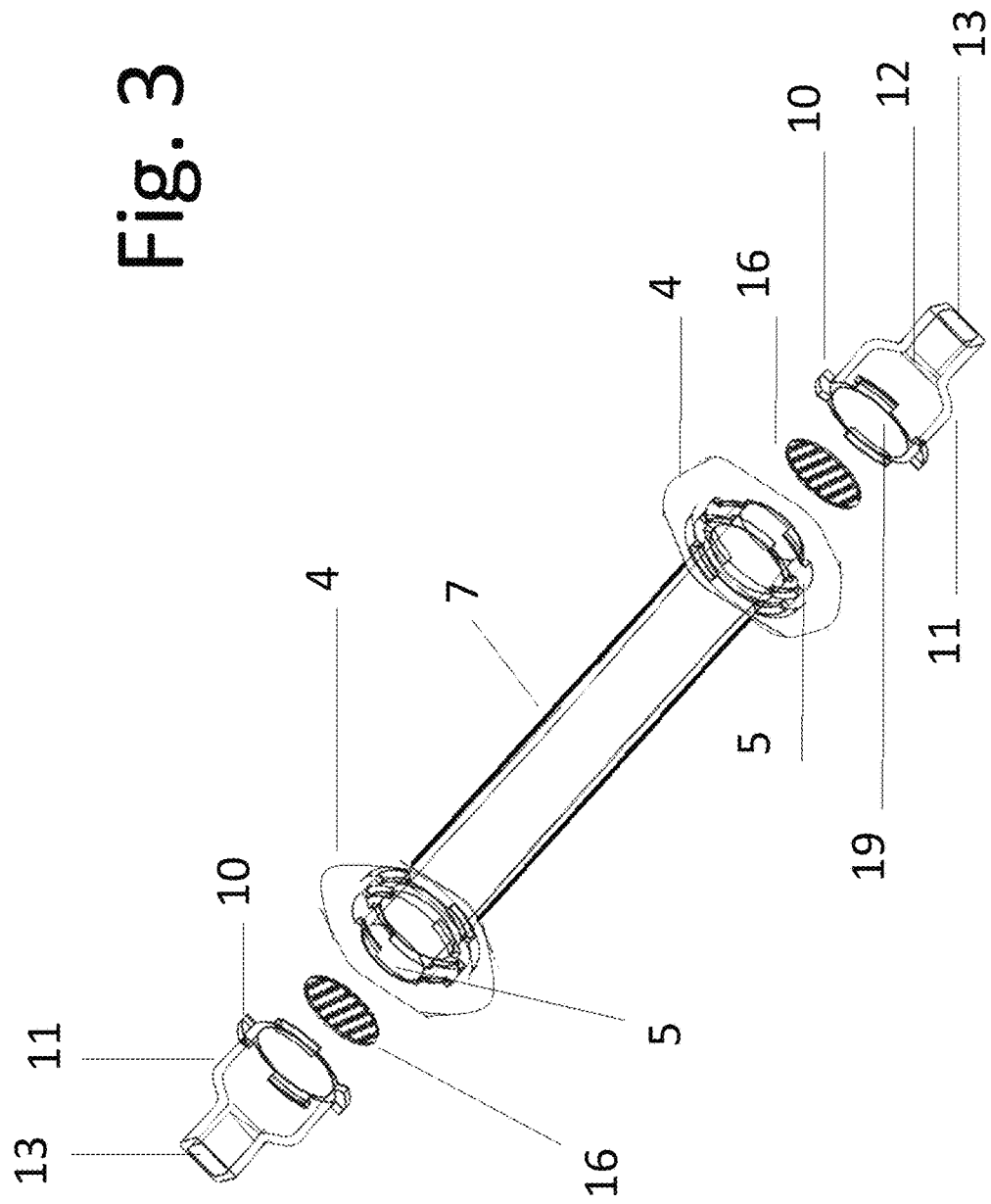
FIG. 3 is a perspective view of the filter-funnel assembly of the present invention receiving a filter in its basket and a detachable cuvette.

FIG. 1 provides a perspective view of the infusion chamber capped at one end with a filter-funnel 11 assembly holding a filter 9 and a spectrometry cuvette 15, and at the other end, receiving a plunger 2. FIG. 2 provides an exploded, perspective view of the infusion chamber 7 capped at both ends with filter-funnel 11 assemblies carrying coin-shaped rubber stoppers 16 to create a sealed chamber in which the extraction reaction can occur. The filter-funnel 11 assembly contains a meshed basket 12 at one end and a tapered funnel at the other end. The basket end 12 holds the rubber stopper 16 in place during an extraction reaction and holds a filter 9 in place to allow separation of residual sold matter from solvent at the conclusion of an extraction reaction. The properties of the meshed basket 12, including the material from which it is composed and the size of the mesh's pores, modulate the solutes extracted from the extraction mixture. After an extraction reaction, the rubber stopper can be replaced with a filter which holds back residual solid matter while the pressure created by advancing the plunger 2 at the other end forces cannabinoid-containing solution through the filter and funnel and into a spectrometry cuvette 15, which can also function as a spout when its cap 18 is removed. The filter-funnel component's tapered rims 10, which consist of tapered protrusions from the perimeter of the filter-funnel's orifice 17, are complementary to the apertures 5 in the infusion chamber's base 4. The filter-funnel 11 component's tapered rim 10, and the complementary defects in the infusion chamber's base, allows the filter-funnel component to be securely attached and detached with a twisting motion. Secure attachment of the filter-funnel component prevents leakage of mixture during extraction and filtration, and rapid detachment facilitates washing and rinsing of the apparatus in between samples.

The plunger component has a rubber end 3 to allow smooth and complete evacuation of the infusion chamber's contents following an extraction reaction. It is sized to completely occlude the infusion chamber at one end to prevent leakage of solvent.

Figure 4:
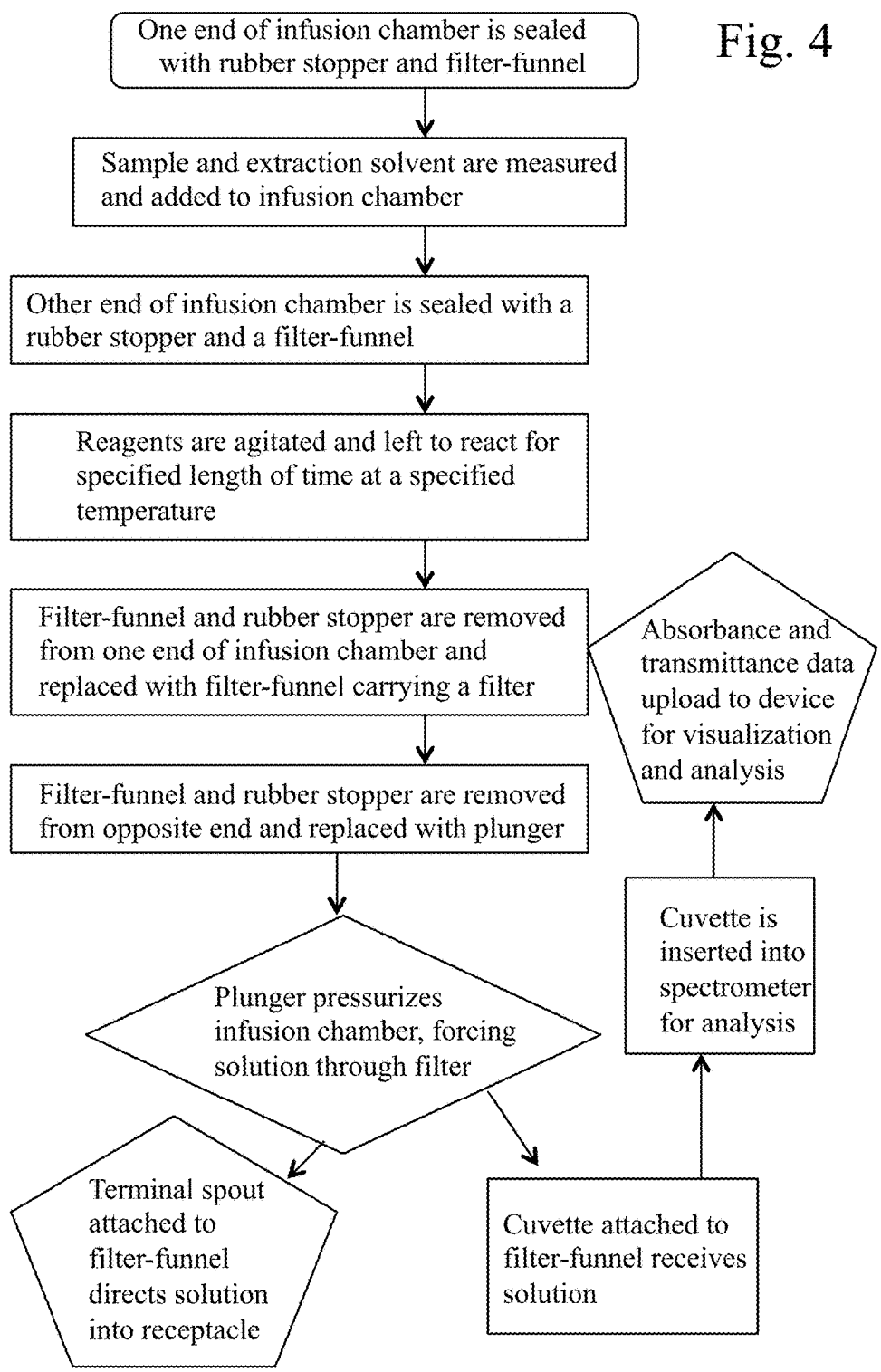
FIG. 4 is a flowchart illustrating the sequence of events in the process of preparing and analyzing a sample using the present invention and light spectrometry.
Figure 5:
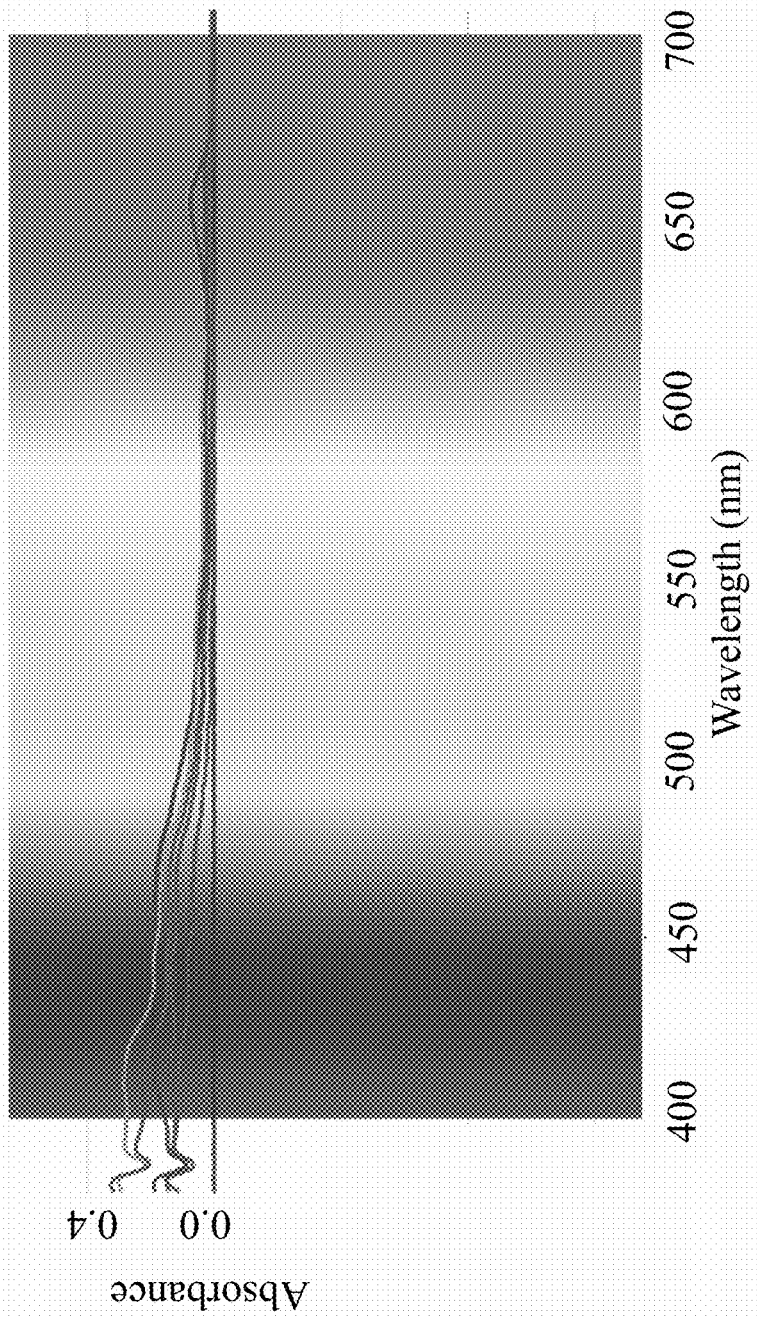
FIG. 5 is a photograph of the absorbance spectra of five distinct varieties of *cannabis* flower extracted using the present invention.

Light spectrometry has many different uses in analytical chemistry. Light from the ultraviolet, visible, and infrared spectrum has been used to measure absorbance and transmittance of various chemical compounds which differ in the way and extent to which they interact with light energy. Light spectrometry allows the identification of compounds and allows the quantification of concentrations of solutions. The flowchart in FIG. 4 demonstrates the individual steps comprising the process of conducting and analyzing a sample, which this invention serializes.

I claim:

1. An extraction infusion testing device for facilitating chemical extraction of compound comprising:
    a sealed infusion chamber including graduated markings for volume; said infusion chamber comprising including an inlet for introducing a solvent and sample, mixing and agitating in said chamber; extracting with a solvent and separating through a serial filtration funnel assembly and an outlet which is operative connection with a detachable funnel assembly, in-line spectrometry cuvette, said infusion chamber including capping;
    said funnel assembly comprising a pliable filter funnel component including a mesh basket, a filter and rubber stopper wherein said funnel delivers filtered extractant into a detachable spout or a detachable light spectrometry cuvette, wherein said filter-funnel assembly attaches to both ends of said infusion chamber by aligning tapered ledges extending from the perimeter with the infusion chamber; wherein the filter-funnel assembly is twistable; and wherein the rubber stopper provides a waterproof and pressurization upon attachment to the chamber and filter assembly;
    said apparatus further includes a plunger assembly received by said infusion chamber for creating a seal between the plunger tip and infusion chamber to pressurize the infusion chamber to apply a force upon depression of said plunger to force said sample, solvent extractant through said filter funnel assembly;
    and wherein said detachable spout is insertable into the funnel filter assembly and from the infusion chamber which is connection with a receptacle or cuvette.

\* \* \* \* \*